United States Patent [19]

Solacoff

[11] Patent Number: 5,132,518

[45] Date of Patent: Jul. 21, 1992

[54] APPARATUS FOR WARMING COLD MEDICAL DIAGNOSTIC INSTRUMENTS SUCH AS STETHOSCOPES

[76] Inventor: K. K. Solacoff, 470 Shafer Dr., Upper Sandusky, Ohio 43351

[21] Appl. No.: 654,294

[22] Filed: Feb. 12, 1991

[51] Int. Cl.$^5$ ............ A61B 7/02; H05B 1/00; F26B 25/14

[52] U.S. Cl. ............ 219/385; 34/201; 34/202; 34/239; 34/243 R; 181/131; 181/137; 219/201; 219/220; 219/242; 219/521; 312/207; 392/416; 392/418

[58] Field of Search ............ 219/200, 201, 219, 214, 219/218, 242, 385, 386, 521, 552, 220; 312/206, 207, 210, 236; 34/201, 202, 239, 243 R; 181/131, 137; 392/416, 418

[56] References Cited

U.S. PATENT DOCUMENTS

| | | | |
|---|---|---|---|
| 1,550,334 | 8/1925 | Baxter | 219/521 X |
| 1,581,426 | 4/1926 | Coons | 34/202 |
| 1,919,081 | 7/1933 | Weisswasser | 219/521 X |
| 1,992,564 | 2/1935 | Amdur | 312/207 X |
| 2,180,213 | 11/1939 | Peake | 219/521 X |
| 2,417,802 | 3/1947 | Longstreet | 219/201 X |
| 2,471,884 | 5/1949 | Monnot | 219/218 |
| 2,527,049 | 10/1950 | Aagesen | 219/521 X |
| 2,527,101 | 10/1950 | Maddox | 219/552 X |
| 2,644,072 | 6/1953 | Aruth | 219/521 |
| 2,713,112 | 7/1955 | Mills et al. | 219/521 |
| 2,864,932 | 12/1958 | Forrer | 219/521 X |
| 2,999,145 | 9/1961 | Espenhain | 219/552 X |
| 3,766,361 | 10/1973 | Swinyar et al. | 219/521 |
| 4,007,806 | 2/1977 | Nobles | 219/201 X |
| 4,241,290 | 12/1980 | Folland | 34/202 X |
| 4,278,870 | 7/1981 | Carleton et al. | 219/521 X |
| 4,867,268 | 9/1989 | Ulert | 181/131 X |
| 4,910,386 | 3/1990 | Johnson | 219/521 X |

FOREIGN PATENT DOCUMENTS

| | | | |
|---|---|---|---|
| 179171 | 5/1986 | European Pat. Off. | 219/201 |
| 463732 | 8/1928 | Fed. Rep. of Germany | 219/242 |
| 2627976 | 9/1989 | France | 219/201 |
| 672412 | 11/1989 | Switzerland | 219/201 |
| 1273628 | 5/1972 | United Kingdom | 219/521 |

*Primary Examiner*—Anthony Bartis
*Attorney, Agent, or Firm*—Douglas L. Tschida

[57] ABSTRACT

An apparatus for warming medical instruments, such as a stethoscope, includes a wall mountable, multi-walled, vented housing having a front access opening closed by a hinged translucent panel and an open bottom. A reflective, flexible metal liner having a lower portion overlying the open housing bottom reflects radiant heat from an electric lamp heat source in the housing toward an instrument to be heated vertically positioned in a support formed in the lower portion of the liner and aligned with a slot in the lower portion leading to the access opening. The heat source is thermostatically controlled.

13 Claims, 3 Drawing Sheets

APPARATUS FOR WARMING COLD MEDICAL DIAGNOSTIC INSTRUMENTS SUCH AS STETHOSCOPES

BACKGROUND OF THE INVENTION

The present invention relates to heating assemblies and, in particular, to an assembly for warming medical instrumentation, such as a stethoscope.

An inconvenience to many medical practitioners and corresponding irritation to the patient occurs during any examination which requires contacting the patient with cold diagnostic instruments, such as a stethoscope. Although the examination procedure may be painless, an instinctive flinching reaction occurs with the first touch of a relatively cold instrument. This reaction may be exagerated due to patient anxiety.

That is, the instrumentation is typically maintained at room temperature, while the patient's body temperature may be some 20 to 40 degrees higher. The relative temperature differential thus tends to induce a skin reaction such as "goose bumps". More commonly, however, the patient flinches or pulls away from contact with the instrument, thus necessitating a firm hand hold on the patient. Otherwise, the instrument must be positionally readjusted to the patient with further patient discomfort.

The thermal differential can be reduced if the practitioner contains the stethoscope within his/her lab coat or if the instrument is held briefly within the hand prior to use. Such practices are not commonly performed. Also, with the modernization of most medical practices, each examination room is typically outfitted with separate sets of diagnostic instruments, for example, stethoscope, blood pressure cuff, oxygen equipment and the like and the practioner may therefore not even carry a stethoscope. Economic pressures to maximize patient loading, also minimizes the time spent with each patient, which further adds to the formality of routine examinations and heightens patient anxiety. Small details, such as pre-warming diagnostic instruments can thus take on added significance to the patient.

Except for the foregoing warming methods, Applicant is unaware of any dedicated device for economically performing the same function. Although sterilizers, or other elaborate equipment used during intrusive procedures may obtain a similar result, Applicant through his numerous years of practice is unaware of any low cost, dedicated device intended for use with diagnostic equipment.

SUMMARY OF THE INVENTION

Accordingly it is a primary of the present invention to provide means for pre-warming equipment exhibiting a thermal differential relative to the operator or subject being contacted with the instrument.

It is a further object of the invention to provide an assembly for warming stethoscopes and other medical, dental instruments or the like to minimize and/or prevent voluntary and involuntary patient jerk or flinch reactions.

It is a further object of the invention to provide an assembly for encasing and supporting the instrumentation from a variety of stationary surfaces.

It is a further object of the invention to provide a portable assembly.

It is a yet further object of the invention to provide a thermally controlled assembly.

Various of the foregoing objects, advantages and distinctions of the invention are particularly obtained in one present construction. This assembly comprises a multi-walled, wall mountable, vented housing which supports a hinged translucent front panel. A reflective, flexible metal liner is secured to the inner wall surfaces to reflect radiant heat from a lamp heat source. A lower portion of the liner includes a cutout region for vertically supporting a portion of the stethoscope relative to a vertical support member and grooved channel. The support shape and spacing relative to the translucent cover are determined to facilitate instrument removal and venting of the housing interior. A thermostat may be provided to obtain additional thermal control.

In a portable, battery powered assembly, a molded housing includes a battery storage compartment and a resilient instrument support shelf which retains the instrument in contact and/or close proximity to a heated pad. The heated pad particularly comprises a serpentine conductor secured to at least one interior wall. The conductor is overlaid with an appropriate thermal transfer material.

Still other objects, advantages and distinctions of the invention, as well as the detailed construction of the foregoing assemblies, is provided hereinafter in the following description with respect to the appended drawings. Before referring thereto, it is to appreciated the description is made by way of presently considered embodiments only and should not be interpreted in limitation of the scope of the invention. To the extent modifications and improvements have been considered, they are described as appropriate. Otherwise, the invention should be interpreted within the scope of the following appended claims.

DESCRIPTION OF THE PREFERRED EMBODIMENTS

Figure 1:
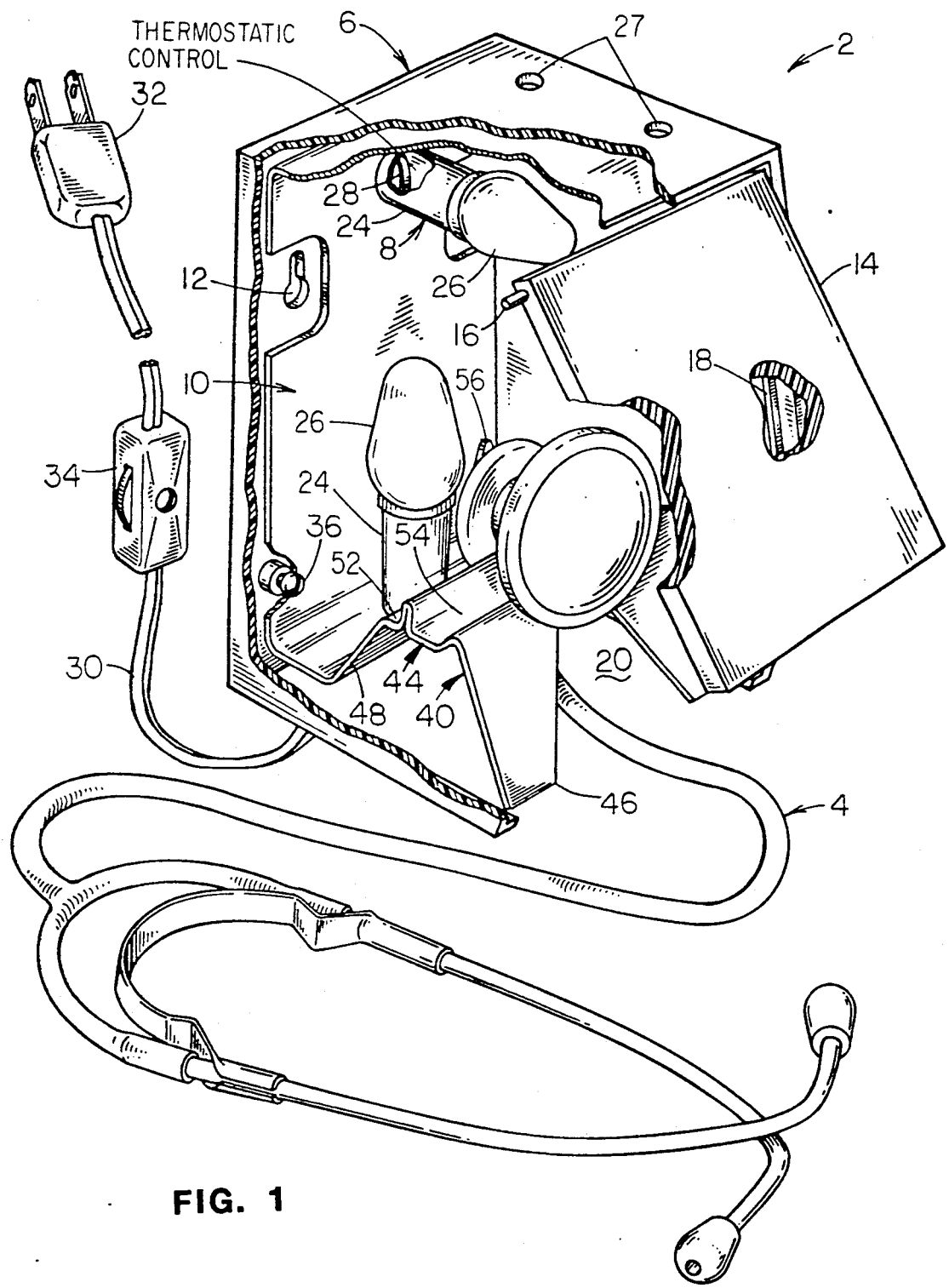
FIG. 1 is a perspective drawing, shown in partial cutaway, a radiant heat lamp assembly.

Referring to FIG. 1, a perspective drawing is shown in partial cutaway of an assembly 2 which finds application for preheating a stethoscope 4 or similar diagnostic instrumentation. The assembly 2 generally comprises a vented housing 6 which contains a heat source 8 and a further subassembly 10 for supporting a particular instrument in relation to the heat source 8 and housing 6.

The housing depicted is constructed as a multi-walled assembly which walls are separately attached to one another. The housing may alternatively be formed as an integral unit. Wood or suitably formed, heat tolerant metal, plastics, or polymer composites may be used to these ends. Depending upon the mounting circumstance, appropriate attachment devices are included. Key hole slots 12 are presently provided, although apertured hangers, mating lengths of Velcro or the like can be attached or formed into the housing. Varieties of other mating fasteners can also be included to support the housing from a building wall or other support surface.

Secured to a front surface of the housing 6 is a translucent cover panel 14. The cover 14 is supported at a pair of pivots 16 which extend from upper peripheral edges of the cover 14 and mate with holes let into the housing. Stop projections 18 extend from the lower housing interior walls to limit the cover travel.

Otherwise, a space or cutout 20 is provided between the bottom cover edge and a reflective support assembly 22. The cutout 20 is provided to vent the interior of the housing 6, as well as to facilitate removal of the instrument 4 without lifting the front cover 14. The front cover 14 otherwise may be rotated during withdrawal of the instrument 4 or to access; one or more internally mounted sockets 24 and lamps 26 which act as the heat source 8. Additional vent apertures 27 may be provided within the housing walls to maintain desired interior temperatures without experiencing overheating.

Overheating may also be prevented with a thermostatic control. For example, a bimetal sensor can be mounted within the housing 6 to appropriately switch power to the lamp 26 and thereby regulate the interior temperature. A flexible bimetal coil element 28 is shown, which is coupled in series with the supply power inside the socket 24, to suitably couple power to the lamp with changing housing temperatures. Where AC power is used, a power cord 30 is provided which contains an appropriate plug end 32 and an on/off switch 34. The cord is supported to the housing through a bushed aperture (not shown).

Figure 2:
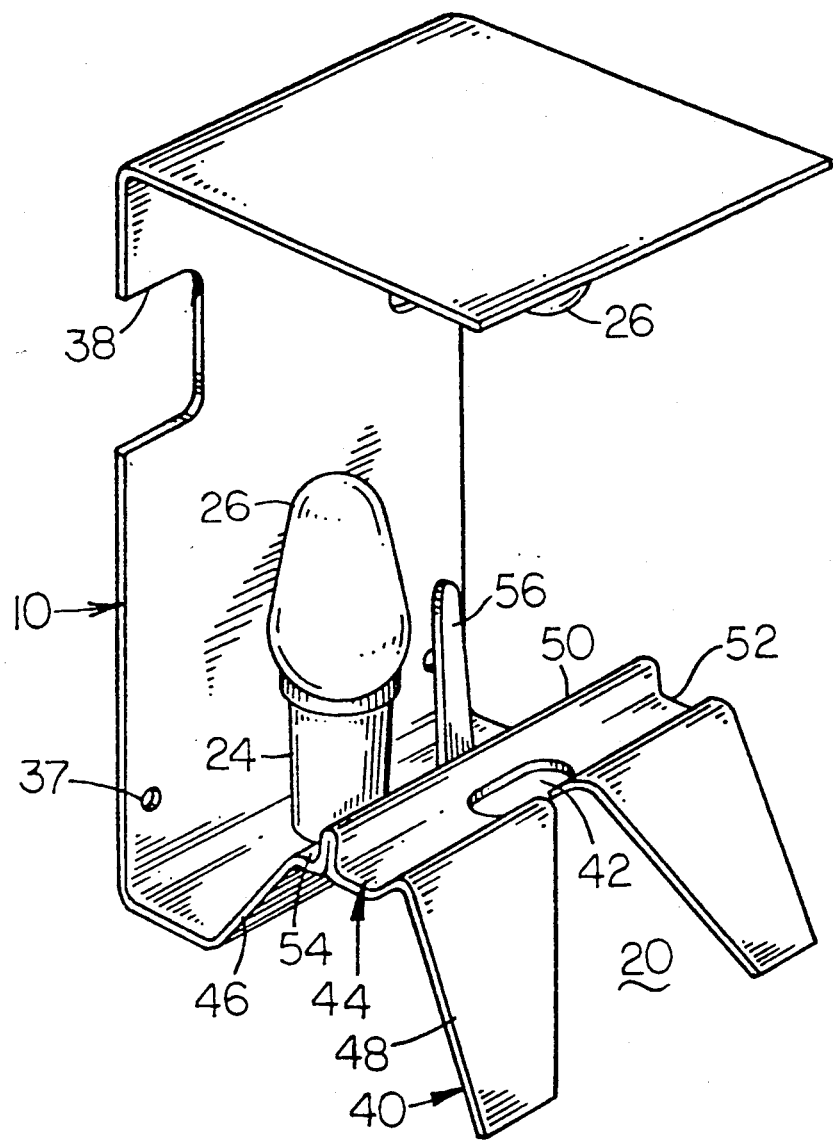
FIG. 2 is a detailed perspective drawing of the reflective liner and instrument support of the assembly of FIG. 1.

With further attention to FIG. 2, a detailed perspective drawing is shown of the metal, heat-reflective liner 10 that is supported within the housing 6. The liner 10 particularly comprises a C-shaped member, when viewed in side profile, that is secured with screws 36 or the like to the rear and top interior wall surfaces of the housing 6. Cutouts 38 are provided to accommodate the keyhole slots 12. The liner 10 supports the sockets 24 that receive the heat lamps 26. Although two sockets 24 are shown, more or less may be provided, as desired and depending upon the type of instrumentation being heated and size of the housing. The depicted stethoscope housing is approximately four inches deep by four inches wide bye six inches tall and requires a single lamp.

Whereas a metal formed liner 10 is included to prevent any risk of fire and distribute the heat, it is to be appreciated varieties of other heat resistant, reflective materials may be substituted. Alternatively, the housing 6 itself may be constructed from a heat resistant material. Varieties of thermal insulating techniques may also be employed.

A lower, resilient liner projection 40 serves as the bottom of the housing 6. The upper end of the cutout 20 terminates in a support configured to include an ovular cutout portion 42, where the stethoscope is supported. Access to the support portion 42 and the interior of the housing is facilitated via the bending of the projection 40 to provide a raised support shelf 44 which is suspended between front and aft surfaces 46 and 48. The bending of projection 40 not only enhances housing access but also permits a certain amount of flexing of the projection 40. This prevents damaging the instrument or pulling the housing from the wall, in the event the stethoscope 4 is not fully released from the projection 40 during removal.

Aligned with the support cutout 42 at the shelf 44 and on opposite sides of a raised rib 50 are transverse grooves or depressions 52 and 54. The aft depression 54 receives a lower edge of the stethoscope 4 to partially capture same. A vertical upright member 56, mounted immediately posterior of the cutout 42, provides a surface against which the instrument leans. Alternatively, U-shaped resilient fingers (not shown) may project from the depression 54 or surface 48 to capture and/or restrain the instrument. Where multiple lamps 26 are used, the upright 56 also acts as a spacer to prevent contact between the instrument and lamp 26.

Figure 3:
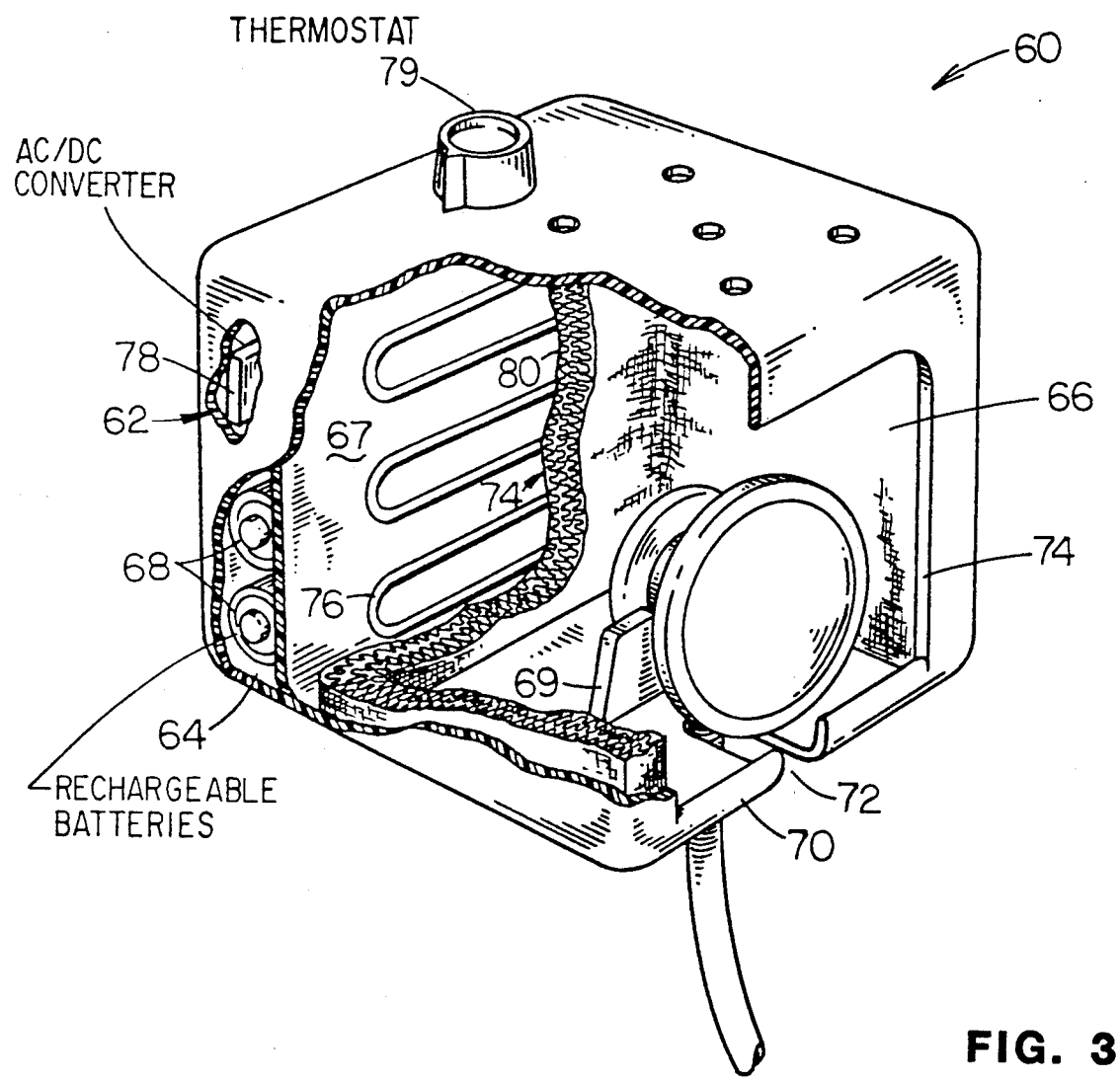
FIG. 3 is a perspective drawing, shown in partial cutaway, of a battery powered warmer including a heating pad.

Referring to FIG. 3, a battery powered warming assembly 60 is shown. This assembly includes a formed plastic housing 62 which is molded to most advantageously contain and store a particular instrument. A rear compartment 64 is separated from a front warming compartment 66 by a wall 67 and contains batteries 68.

The warming compartment 66, again, provides an interior cavity space for receiving the instrument 4. The instrument 4 is particularly supported on a multi-fingered, U-shaped projection 69 which extends from a bottom wall 70, at the aft end of a slot 72 and forward of an active heating pad assembly 74.

The top and side walls of the housing 62 otherwise are formed to surround the instrument 4, while the front wall provides a cutout, access window 74. The depth of the warming compartment 66 is sufficiently sized to permit the removal of the instrument by merely lifting and pulling the instrument forward.

The heating pad assembly 74, otherwise, is comprised of a serpentine heating element 76 which is appropriately bonded to the wall 67. The size, length and watt requirements of the element 76 are selected to accommodate a predetermined battery life or re-charge cycle, where rechargeable batteries are used. The assembly 60 may also contain AC/DC conversion circuitry 78 within the battery compartment 64 or remote therefrom for use as a permanent assembly. A thermostatic control 79 regulates the temperature of the housing interior.

Supported in overlying relation to the heating element 76 is a thermal transfer pad 80 which can be constructed from a variety of materials or composites. For example, a metal loaded fabric or other pliable heat transmissive material may be used. Preferably, however, the material should exhibit a high heat transmissivity, without burning or discoloring over-time. Depending upon the material, the instrument 4 may be mounted to directly contact the pad 74. It is to be further appreciated that still other radiant heating assemblies may be used which may include a fan for providing convection heating or the like.

While the present invention has been described with respect to variously considered constructions and modifications thereto, still other modifications and improvements may suggest themselves to those skilled in the art. Accordingly, the invention should be interpreted to include all those equivalent embodiments within the spirit and scope of the following claims.

What is claimed is:

1. Instrument warming apparatus comprising:
   (a) a multi-walled housing defining an interior cavity and having a first aperture through one wall communicating with said cavity and including a reflective liner which inwardly directs heat away from the housing walls, and wherein a portion of said liner mounts adjacent said first aperture and includes a slot and support means aligned therewith for receiving and supporting an instrument admitted to said cavity; and (b) thermal means for maintaining the interior of said cavity at a predetermined temperature and whereby said instrument may be pre-warmed to said temperature.

2. Apparatus as set forth in claim 1 wherein said thermal means comprises a radiant heat source.

3. Apparatus as set forth in claim 2 wherein said linear reflects the radiant heat onto said instrument.

4. Apparatus as set forth in claim 2 wherein said radiant heat source comprises at least one incandescent light bulb.

5. Apparatus as set forth in claim 4 wherein said first aperture comprises an open housing bottom and wherein said housing includes a second aperture communicating with said cavity and means for coupling a cover to said housing adjacent said second aperture to permit access to the cavity and the support means upon exposing the second aperture.

6. Apparatus as set forth in claim 5 wherein said cover is translucent and including means for hinge mounting said cover to the housing and stop means for limiting the travel of said cover relative to the housing.

7. Apparatus as set forth in claim 6 including means for supporting said housing from a stationary support surface.

8. Apparatus as set forth in claim 1 wherein said first aperture extends through the bottom of said housing.

9. Apparatus as set forth in claim 8 wherein a portion of said liner overlies the first aperture and includes forward and aft wall surfaces which taper upwardly to a flattened region, wherein the slot extends from an edge of the forward wall surface into the flattened region and said flattened region includes a vertically projecting rail and said aft surface includes a vertically projecting support, and wherein the rail and vertical support are arranged to support said instrument in upright alignment.

10. Apparatus as set forth in claim 1 including means for thermostatically controlling the predetermined temperature.

11. Apparatus as set forth in claim 1 wherein said housing includes means for venting the interior of said housing.

12. Instrument warming means comprising:

(a) a multi-walled housing defining an interior cavity and including an open bottom and an aperture in a wall adjacent the open bottom, said aperture permitting the insertion and retraction of an instrument into the cavity and wherein said cavity includes a radiant liner mounted in thermal communication with a heat source means supported from at least one wall of said housing and wherein a portion of said liner overlies the open bottom and includes forward and aft wall surfaces which taper upwardly to a flattened region, wherein a slot extends from an edge of the forward wall surface into the flattened region and said flattened region includes a vertically projecting rail and said aft surface includes a vertically projecting support, and wherein the rail and vertical support are arranged to support said instrument in upright alignment; and (b) means for thermostatically applying power to said heat source means for maintaining a supported instrument at a temperature approximating that of human skin.

13. Apparatus as set forth in claim 12 wherein said heat source comprises an incandescent light bulb.

* * * * *